(12) United States Patent
Shiber

(10) Patent No.: US 7,104,966 B2
(45) Date of Patent: Sep. 12, 2006

(54) GUIDEWIRE SYSTEM WITH EXPOSED MIDSECTION

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 452 days.

(21) Appl. No.: 10/620,740

(22) Filed: Jul. 16, 2003

(65) Prior Publication Data

US 2005/0015021 A1    Jan. 20, 2005

(51) Int. Cl.
*A61B 5/00* (2006.01)
*A61B 17/22* (2006.01)
*A61M 25/00* (2006.01)
*A61D 1/02* (2006.01)

(52) U.S. Cl. ...................... 600/585; 606/159
(58) Field of Classification Search ........ 600/433–435, 600/566, 567, 585; 604/22, 93.01, 164.01, 604/164.09, 164.13; 606/159
See application file for complete search history.

(56) References Cited

U.S. PATENT DOCUMENTS

| | | | |
|---|---|---|---|
| 3,614,953 A | 10/1971 | Moss | |
| 3,683,891 A | 8/1972 | Eskridge et al. | |
| 3,749,085 A | 7/1973 | Willson et al. | |
| 4,030,503 A | 6/1977 | Clark, III | |
| 4,368,730 A | 1/1983 | Sharrock | |
| 4,653,496 A * | 3/1987 | Bundy et al. | 606/159 |
| 4,706,671 A * | 11/1987 | Weinrib | 606/159 |
| 4,728,319 A | 3/1988 | Masch | |
| 4,732,154 A | 3/1988 | Shiber | |
| 4,754,755 A | 7/1988 | Husted | |
| 4,772,258 A | 9/1988 | Marangoni et al. | |
| 4,784,636 A | 11/1988 | Rydell | |
| 4,790,812 A | 12/1988 | Hawkins, Jr. et al. | |
| 4,857,046 A | 8/1989 | Stevens et al. | |
| 4,883,458 A | 11/1989 | Shiber | |
| 4,886,490 A | 12/1989 | Shiber | |
| 4,898,575 A | 2/1990 | Fischell et al. | |
| 4,909,781 A * | 3/1990 | Husted | 604/22 |
| 4,923,462 A | 5/1990 | Stevens | |
| 4,935,025 A * | 6/1990 | Bundy et al. | 606/180 |
| 4,979,939 A | 12/1990 | Shiber | |
| 5,018,530 A | 5/1991 | Rank et al. | |
| 5,047,040 A | 9/1991 | Simpson et al. | |
| 5,078,723 A | 1/1992 | Dance et al. | |
| 5,135,531 A * | 8/1992 | Shiber | 606/159 |
| 5,423,799 A | 6/1995 | Shiu | |
| 5,443,443 A | 8/1995 | Shiber | |
| 5,488,958 A | 2/1996 | Topel et al. | |
| 5,490,859 A | 2/1996 | Mische et al. | |
| 5,501,694 A | 3/1996 | Ressemann et al. | |
| 5,792,157 A | 8/1998 | Mische et al. | |
| 5,836,868 A | 11/1998 | Ressemann | |
| 6,251,121 B1 | 6/2001 | Saadat | |
| 6,371,928 B1 | 4/2002 | Mcfann | |
| 6,406,442 B1 | 6/2002 | McFann | |
| 6,500,185 B1 | 12/2002 | Mathews et al. | |
| 6,740,096 B1 * | 5/2004 | Teague et al. | 606/127 |

* cited by examiner

*Primary Examiner*—Max F. Hindenburg
*Assistant Examiner*—Michael Apanius
(74) *Attorney, Agent, or Firm*—Samuel Shiber

(57) ABSTRACT

A flexible guidewire system with an exposed midsection, for crossing an obstruction located in a patient's vessel, comprising a flexible pilot wire and a flexible casing having a distal and proximal portions slidable and rotatable over the pilot wire, at least a distal portion of the casing being a helical wire gated at its distal end, and a coupling for connecting the casing to a drive means.

15 Claims, 5 Drawing Sheets

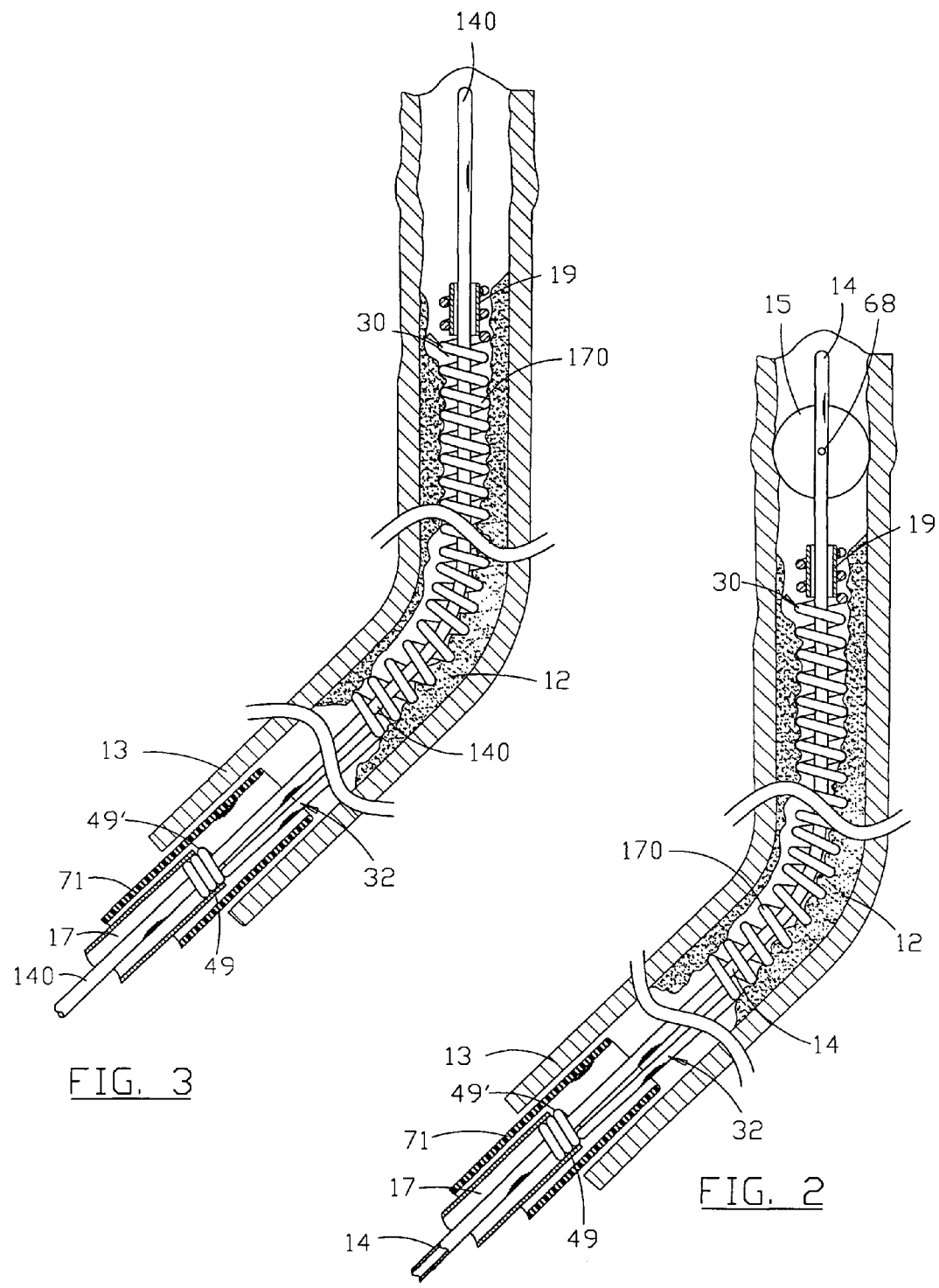

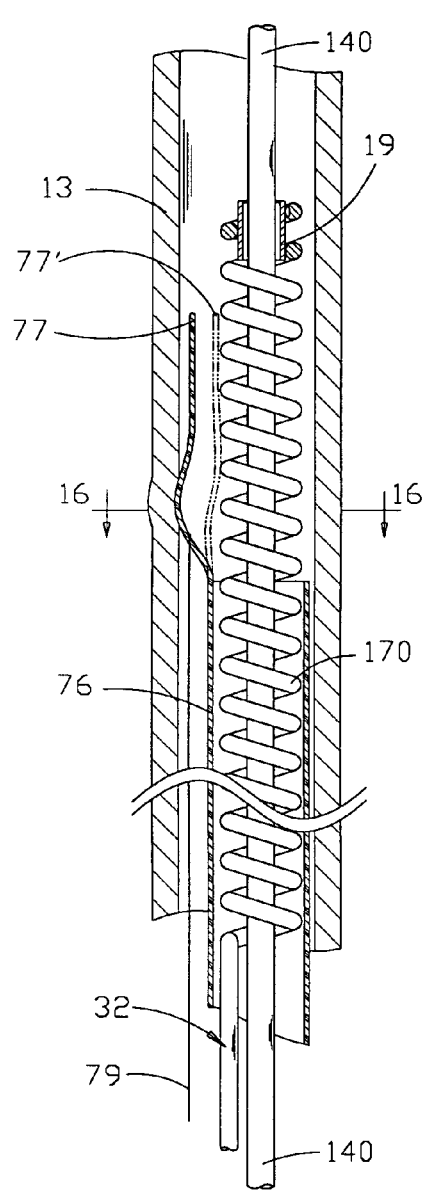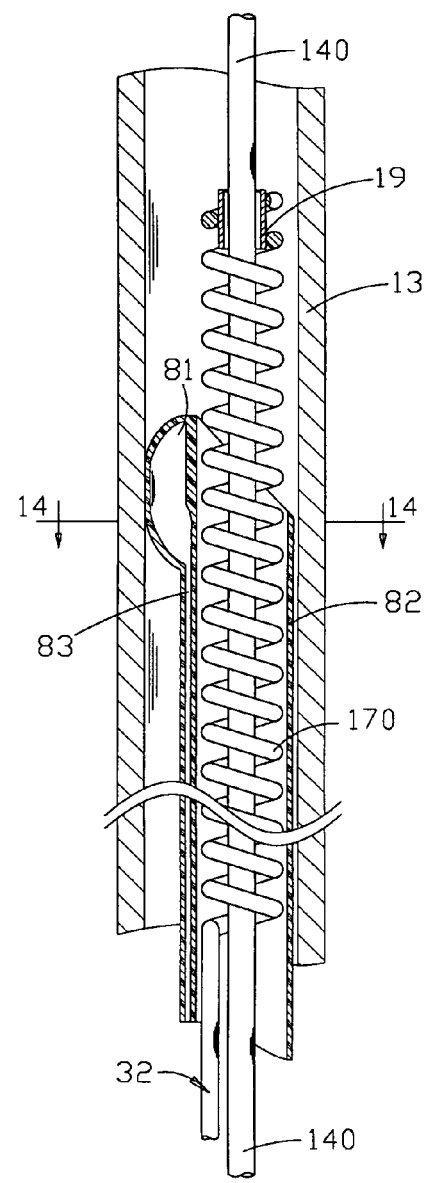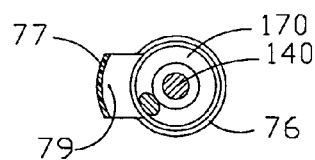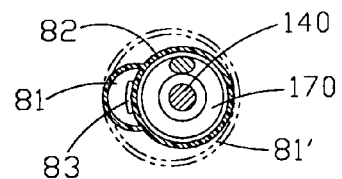
FIG. 15
FIG. 13
FIG. 16
FIG. 14

GUIDEWIRE SYSTEM WITH EXPOSED MIDSECTION

BACKGROUND AND OBJECTIVES OF THE INVENTION

With age a large percentage of the population develops atherosclerotic and thrombotic obstructions resulting in partial or total occlusions of blood vessels in various parts of the human anatomy. Such obstructions are often treated with angioplasty or atherectomy catheters and a common preparatory step to such procedures is the insertion of a guidewire through the obstruction.

An objective of the present invention is to provide, simple and reliable flexible guidewire system that comprises a pilot wire and a casing capable of crossing tortuous vasculature and obstructions, particularly tight and total obstructions. A further objective is to facilitate easy removal or insertion of the casing over the pilot wire while the pilot wire remains stationary in the vasculature.

The above and other objectives of the invention will become apparent from the following discussion and the accompanying drawings.

BRIEF DESCRIPTION OF THE FIGURES

FIG. 2 shows a cross sectioned view of a flexible guidewire system with an exposed midsection with a casing in the form of a helical wire where the spacing between its distal coils is gated by a short tube and its proximal coils are attached to a coupling for connecting the casing to drive means. A pilot wire, comprising a hollow tube and an inflatable chamber at its distal end section, serves as a guidewire over which the casing can be slid and rotated.

FIG. 3 shows same embodiment as in FIG. 2 wherein a standard guidewire serves as the pilot wire.

FIG. 13 shows a partially cross sectioned view of a system with an inflatable chamber located at the distal end of a flexible sleeve.

FIG. 14 shows a cross sectioned view of the system shown in FIG. 13, along a line 14—14 marked on FIG. 13.

FIG. 15 shows a partially cross sectioned view of a system with a flexible sleeve having a selectively actuatable tongue at its distal end.

FIG. 16 shows a cross sectioned view of the system shown in FIG. 15 along the line 16—16 marked on FIG. 15.

DETAILED DESCRIPTION OF THE DRAWINGS

Figure 1:
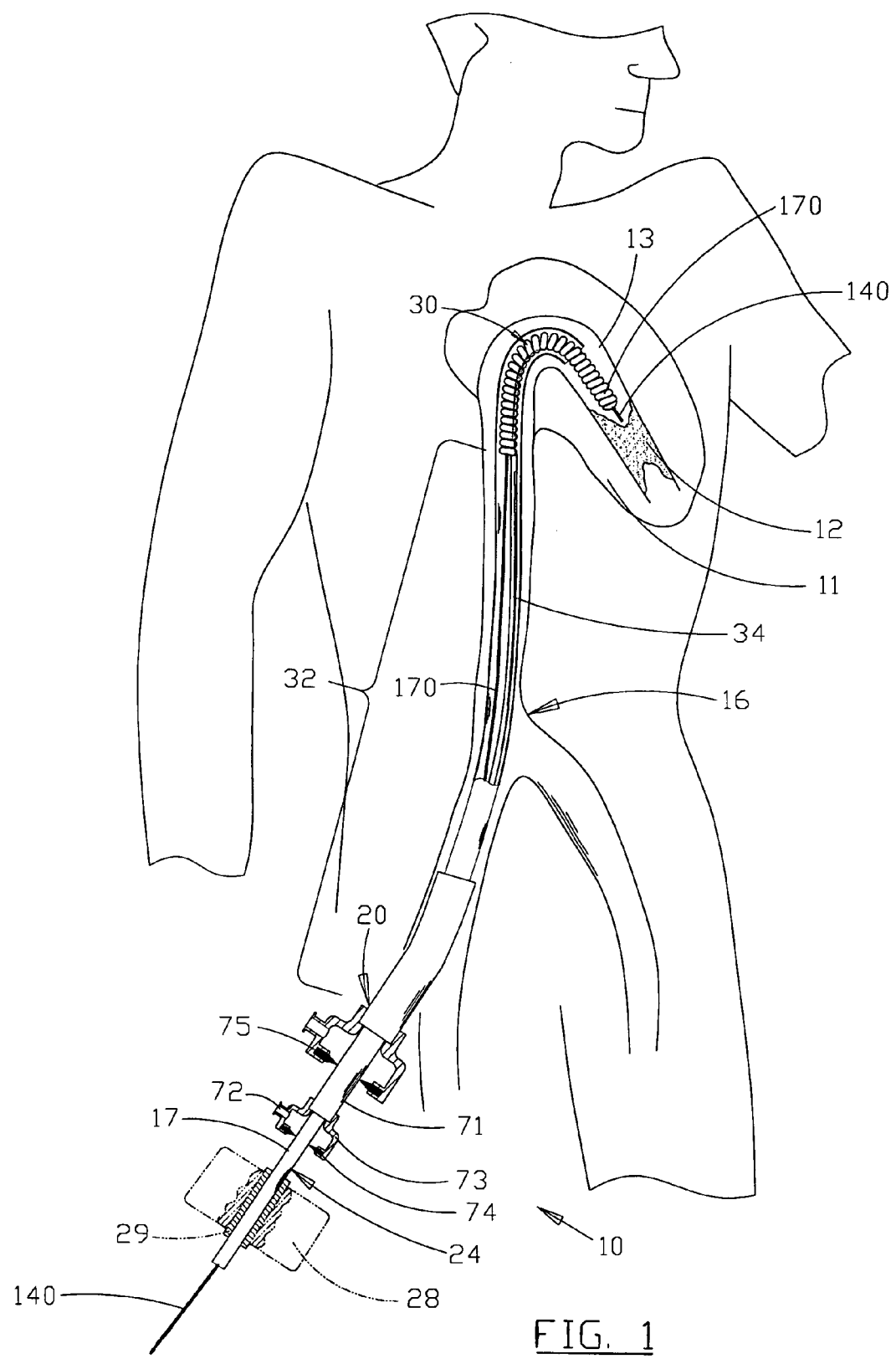
FIG. 1 schematically shows a flexible guidewire system with an exposed midsection for crossing an obstruction in a vessel. The system is inserted at the patient's groin area, through the arterial system of the patient, into his obstructed coronary artery (the anatomy and system's parts are not drawn to scale).

FIG. 1 schematically shows a flexible guidewire system with an exposed midsection 10 for crossing an obstruction 12 located in a patient's coronary vessel 13 serving the heart 11. The system is introduced through the skin into the patient's arterial system 16 through a flexible sleeve 71 that isolates it from the arteries' walls and directs the system to the obstruction site. A nipple 72 is connected to the flexible sleeve through an annular chamber 73 that is attached to the proximal end of the sleeve. The chamber is equipped with a seal 74 which seals around a coupling 17 and communicates fluid entering a nipple 72 through the sleeve into the vessel. Optionally, the distal section of the sleeve is curved, as shown, to direct the system into the vessel and selectively bias it in the vessel towards the obstruction. The sleeve 71 can be inserted into the vasculature through a standard introducer 20 (standard introducers are sold by numerous companies, e.g., TFX Medical, Jaffrey, N.H., or Boston Scientific, Natick, Mass. or Medtronic, Minneapolis, Minn.).

The system comprises elongated parts that can rotate and slide one relative to the other, and their ends which goes further into the vessel shall be referred to as "distal" and their other ends shall be referred to as "proximal"

FIG. 2 shows a guidewire system with an exposed midsection comprising a flexible pilot wire 14 and a flexible casing having a tubular distal portion 30 slidable and rotatable over the pilot wire. The distal portion 30 is made of a helical wire 170 (note also FIG. 1 and note that similar parts are indicated by same numbers throughout the FIGURES) that is gated at its distal end by a tube section 19 that is attached to the helical wire and closes the spacing between its distal coils. Thus the gated distal end of the helical wire keeps the pilot wire inside the helical wire's lumen 21 (note FIG. 5) by preventing the pilot wire from working its way between the coils particularly while the helical wire is rotated.

An elongated thin midsection of the casing 32 is made a substantially straight wire that is a continuation of the wire of which the helical wire 170 is made of and it is disposed alongside to, slidable along and rotatable around the pilot wire 14. The proximal end of the midsection is connected to a proximal tubular coupling 17 that is slidable and rotatable over the pilot wire for rotating and linearly moving the casing over the pilot wire while leaving a section of the pilot that is disposed alongside to the midsection of the casing is exposed to allow the user to hold onto the pilot wire (when it is outside the sleeve 71).

Preferably the proximal end 49' of the midsection 32 is a short helical coil that serves as a strain relief (to prevent the midsection 32 from being bent where it connects to the coupling 17 when the two are inadvertently misaligned) and makes it easier to connect the tubular coupling 17 to the midsection 32 by preferably a weld 49. The coupling serves to connect the casing to drive means that can advance and rotate the casing over the pilot wire in the vessel. To facilitate the linear motion and rotation, the tube 17 has a smooth outside surface 24 that allows it to slide through a seal 74 (note FIG. 1) and rotate without excessive leakage, or if an introducer is used alone without a sleeve, through a seal 75 of the introducer 20. The drive means can simply be a user's hand. Alternatively, an optional motor 28 (shown in FIG 1 in phantom lines) can provide the rotation through its hollow output shaft 29 that is slid over and frictionally engages the coupling 17 while the linear motion is done manually by the physician hand that holds and linearly moves the motor.

The pilot wire 14 that is shown in FIG. 2 is hollow and is equipped with an chamber 15 that is attached to its distal end. The chamber 15 can be inflated and deflated through the hollow flexible pilot wire and an orifice 68 to center the flexible pilot wire in the vessel, to cushion the contact between the flexible pilot wire and the vessel wall, as well as for anchoring it to the vessel wall.

FIG. 3 shows a flexible guidewire system with an exposed midsection wherein the flexible pilot wire is constructed like a standard flexible guidewire 140 (standard guidewires are sold by numerous companies, e.g., TFX Medical or Boston Scientific or Medtronic).

Figure 5:
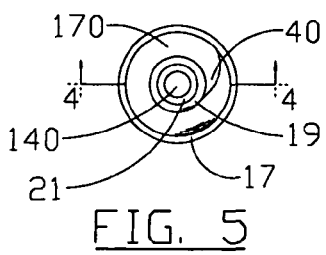
FIG. 5 shows an end view of the helical wire shown in FIG. 4.
Figure 4:
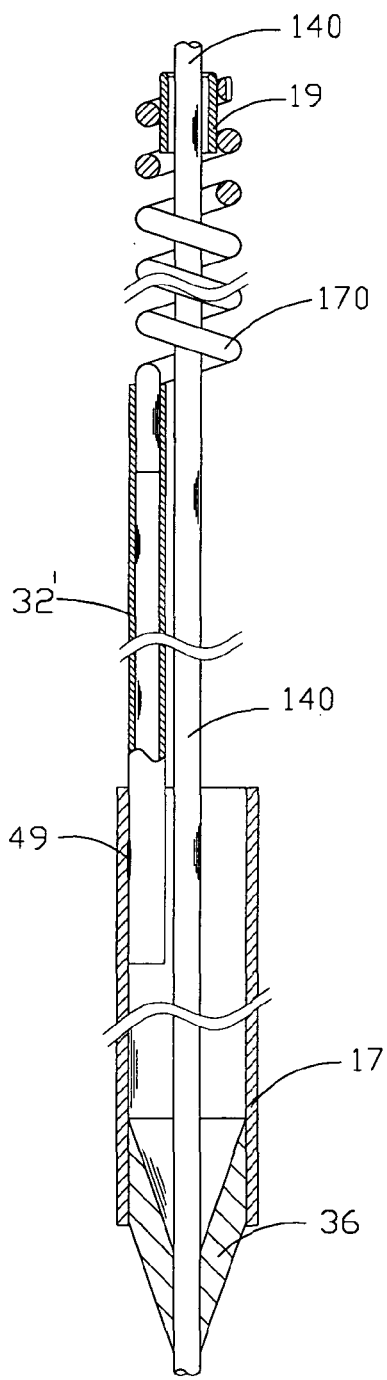
FIG. 4 shows an enlarged partially cross sectioned view (along line 4—4 marked on FIG. 5) of a guidewire system with a midsection 32' made of a thin walled tube.

FIG. 4 shows an enlarged, partially sectioned view (along line 4—4 marked on FIG. 5) of the distal section of the helical wire 170 where the distal entry to the helical wire is gated by the tube 19, preferably made from radio opaque material (for example an alloy comprising gold and/or platinum), attached to the internal diameter of the casing that closes the spacing between its distal coils and keeps the pilot wire inside the casing's lumen 21 (note FIG. 5).

FIG. 5 shows a distal end view of the casing shown in FIG. 4 having a pointed distal end tip 40, adjacent to the tube 19, to ease penetration into the obstruction material. The tip 40 can be manufactured by gradually grinding down the wire to form a smooth inclined plane minimizing trauma that it may cause to the vasculature or the vessel 13.

Figure 6:
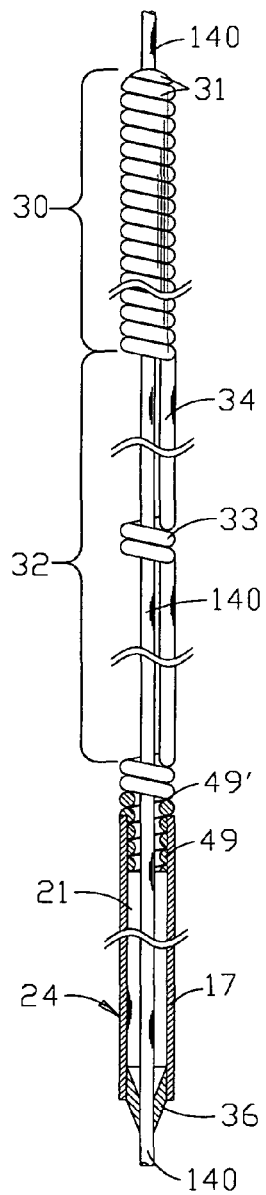
FIG. 6. shows a casing wherein the distal end of the flexible casing is gated by a closely wound coils of the helical wire. The midsection of the flexible casing is made of straight wire section that is a continuation of the wire of the same wire of which the distal end is made of, and it contains a couple of coils to prevent separation of the midsection from the pilot wire. The wire has a round cross section.

FIG. 6 shows a flexible guidewire system with an exposed midsection where the distal end of the casing is gated by closely wound coils 31 of a helical wire 30. The closely wound coils prevent the pilot wire from working its way between the coils when the helical wire is rotated. It also prevents the pilot wire from exiting the helical wire's lumen 21 (note FIG. 7) when the pilot wire is withdrawn into the helical wire and then pushed forward. In addition, the closely wound coils also make the distal portion of the casing more flexible and more radio-opaque. The midsection of the casing 32 is made of a substantially straight wire 34, that is a continuation of the wire of which the helical wire 30 is made of, except that it includes a couple of optional coils 33 for the pilot wire to pass through in order to prevent excessive separation of the midsection from the pilot wire. The wire 34 preferably has a round cross section. The straight midsection in addition to leaving the guide wire 140 exposed provides an increased torsional rigidity (as compared to a helical wire) and thereby it reduces the angular deformation of the midsection under torque.

Coupling 17 has a seal 36 at its proximal end to allow the guidewire 140 to slide and rotate relative to the casing while sealing around it and the seal is preferably designed to close, in the absence of the guidewire passing through it, to prevent blood loss. As can be noted the distal and proximal portions of the casing are tubular, i.e., they defines a lumen in which the pilot wire is contained, where as the midsection is disposed along the pilot wire leaving it exposed.

Figure 6A:
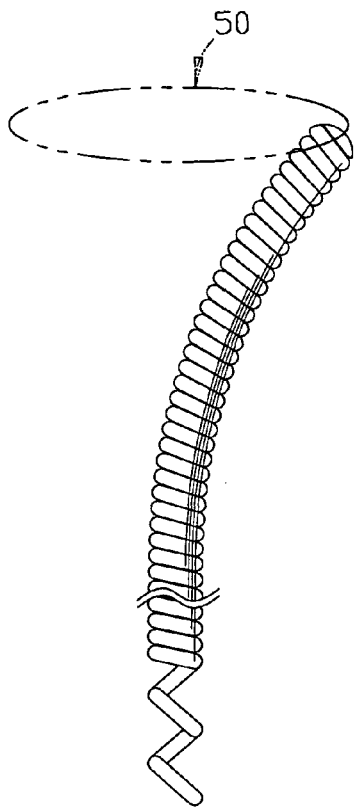
FIG. 6A shows an optional distal portion of the casing shown in FIG. 6 that is curved.

Optionally a distal portion of the casing is curved, as shown in FIG. 6A, so that, as the casing is rotated in order to start penetrating the obstruction, the distal tip moves along a circular pass 50, increasing the probability that it would locate a softer point of the obstruction (once the distal portion starts tunneling through the obstruction it moves along a linear pass).

Figure 7:
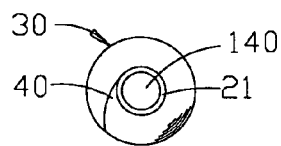
FIG. 7 shows an end view of the helical wire shown in FIG. 6.

FIG. 7 shows an end view of the system shown in FIG. 6.

Figure 8:
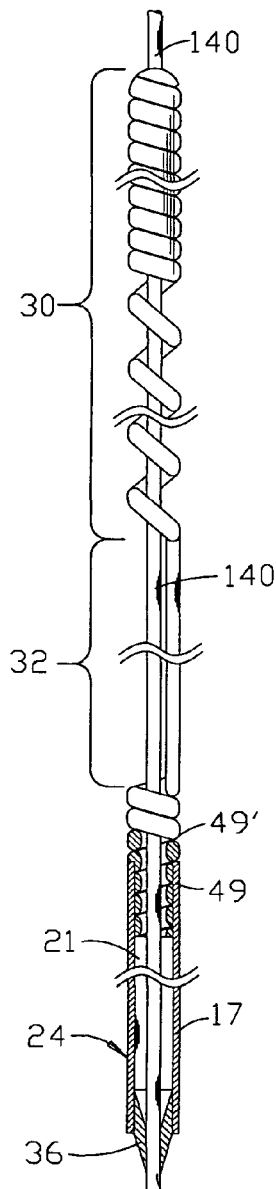
FIG. 8. shows a casing similar to the one shown in FIG. 6 except that the distal portion of the casing has a dual pitch and the wire has a flattened cross section.

FIG. 8. shows a flexible guidewire system similar to the one shown in FIG. 6 except that the wire 30 has a flattened cross section and it is wound on its side, as discussed below.

Figure 9:
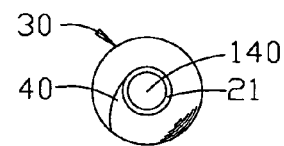
FIG. 9 shows an end view of the helical wire shown in FIG. 8.

FIG. 9 shows an end view of the system shown in FIG. 8.

Figure 10:
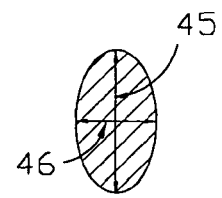
FIGS. 10, 11 and 12 show optional cross sections of flattened wires.
Figure 11:
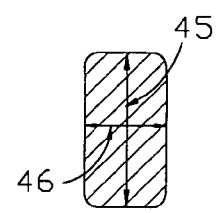
Figure 12:
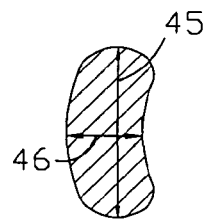

FIGS. 10, 11 and 12 illustrate examples of flattened-wires (the term "flattened-wire", as used in this application, is derived from a common method of manufacturing such wire by flattening a wire with a round cross section between two adjacent rollers). The flattened-wires have a non-round cross section with a long-axis 45, a short-axis 46, and as used in this application, the term "wound on its side" refers to the wire wound with its long-axis being approximately parallel to the helical wire's longitudinal axis.

FIGS. 13 and 14 show side and end views, respectively, of a partially cross sectioned biasing means in the form of an asymmetrical inflatable chamber 81 formed at the distal end of a flexible deflecting sleeve 82 which, when inflated through a channel 83 formed in the sleeve's wall, bears against the vessel's wall, eccentrically biasing the flexible sleeve in the vessel. When deflated, the chamber conforms to the sleeve to minimize interference with its insertion into the vessel. Alternatively, the chamber can be shaped as an asymmetrical toroidal inflatable chamber 81' as shown in FIG. 14 by interrupted lines. This chamber, when inflated, establishes peripheral contact with the vessel's wall and thereby blocks blood flow between the sleeve and the vessel's wall, as well as eccentrically biasing the sleeve (it can be understood that a symmetrical toroidal chamber can be provided for the purpose of blocking the flow around the sleeve while centering the biasing sleeve).

FIGS. 15 and 16 show side and end views, respectively, of a partially cross sectioned flexible sleeve 76 that has a tongue 77 which can be used to bias the sleeve in the vessel. The tongue can be energized against the vessel wall by tensioning a flexible rope 79, moving the tongue from its relaxed position which is shown by a phantom line in FIG. 15 and marked 77' to the position shown in solid lines and marked 77.

OPERATION

FIGS. 1 and 2 illustrate systems, according to the present invention, where a distal portion of the flexible pilot wire is inserted into a curved vessel, and assumes the vessel's geometry. Then a casing, having a distal portion in the form of a helical wire, is inserted through the vasculature over the flexible pilot wire. The casing can be rotated to assist it in advancing over the pilot wire and through curves of the vasculature while the flexible pilot wire safely guides the advancing helical wire 170 through the curved vessel. It should be noted that the rotation of the casing substantially reduces the longitudinal friction between the distal portion of the casing and the guidewire nested in its lumen (assuming that the guidewire is held stationary) as well as longitudinal friction between the distal portion of the casing and its surroundings, i.e., the sleeve (assuming a sleeve is used) and the vessel or vessels through which the casing is advanced. Further, the helical wire is turned in the direction that the coils are wound the rotation is translated to a force that pulls and propels the distal portion of the casing forward in through the vessels. Such pulling force generated at the distal end is significant because in order to deliver to the distal end the same amount of force through a tortuous path (as the path through the coronary vasculature is), a larger push force would be required to be applied to the proximal end of the casing which may exceed the casing's columnar strength.

The method of crossing an obstruction with a system according to the present invention can be done as follows:

inserting a distal end of the flexible pilot wire to the vessel and, while manually holding the pilot wire, inserting over its proximal end the distal portion of the casing, advancing the distal portion of the casing past the proximal end of the pilot wire and then shifting the holding point to an exposed point along the pilot wire, continuing to advance the casing and then inserting the proximal end of the pilot wire into a distal end of a tubular coupling while continuing to hold the pilot wire at a point at which it is exposed, advancing the coupling over the pilot wire until it is past the proximal end of the pilot wire and then shifting the holding point to a point on the pilot wire that is proximal to the coupling, advancing and rotating the casing over the pilot wire by rotating the coupling and thereby threading the distal portion of the casing into the obstruction, beyond the distal tip of the pilot wire, and threading it across the obstruction, advancing the pilot wire across the obstruction.

This method enables the user to first insert the pilot wire, (which can be a standard length guidewire or a variation thereof to test the crossability of the obstruction. To the extent that he has difficulty in crossing the obstruction the user can slip the casing over the pilot wire, while being able to maintain the position or the pilot wire in the anatomy, and have the enhanced crossability of the system according to the present invention.

Withdrawing the casing leaving the pilot wire in place can be done by reversing some of the above steps as follow:

Holding the pilot wire at a point at which it is exposed and withdrawing the coupling and then shifting the holding point to a point on the pilot wire that is distal to the distal portion of the casing, withdrawing the distal portion of the casing leaving the pilot wire in place preparatory to subsequent procedures, for example, angioplasty or atherectomy.

The midsection of the casing is thin and flexible, and it is disposed alongside the pilot wire but it does not surround the pilot wire, leaving the pilot wire exposed (the term exposed as used in this application means that the pilot wire is accessible, when it is out of the sleeve, to gain hold of and keep stationary while the user moves the casing over it). At the same time the thin midsection can transmit force from the coupling to the distal portion of the casing (needed to advance the casing over the pilot wire) when both the pilot wire and casing are in the sleeve as it contains the midsection's tendency to buckle under the compressive load.

As the casing is loaded over the pilot wire, first its distal portion has to be inserted over it, and since the midsection of the casing does not surround the pilot wire the coupling has to be inserted over the pilot wire separately. Obviously it would be easier for the user not to insert the coupling over the guidewire, however it should be noted that rotating the coupling while it is disposed along side the pilot wire will cause the midsection of the casing to become twisted and tangled with the guidewire within few turns. Whereas when both the distal portion of the casing as well as the coupling are inserted over the pilot wire, they both rotate over it and allow the midsection to rotate around the pilot wire without becoming tangled with it (the above discussion use of the term "rotate over" that applies to the rotation of the distal portion and the coupling around the pilot wire and "rotate around" that applies to the midsection).

It is also possible to continue and rotate the casing, after it has been threaded across the obstruction, to increase the helical wire's conveyance action, especially when working in an obstruction with a slurry-like consistency, for example, fresh blood clots.

The sequence of inserting the system's components into the vessel may be varied. Steps may be combined to streamline the procedure or added to improve it and to customize the procedure to the individual characteristics of the obstruction and its location and to the working preferences of the medical staff. For example, the system may be introduced percutaneously through a sleeve and/or an introducer or intra-operatively, i.e., accessing vessel directly while it is exposed surgically. Additionally, a standard guiding catheter, which is either straight or curved may be used as a sleeve or as biasing means to be inserted into the vessel to assist in positioning the system's components in the obstruction site. Further, the pilot-wire and the casing can be pre-nested before they are inserted into the vessel.

Further, a system according to the present invention can have different diameters and lengths depending on the size and site of vessel that it is intended for and on whether the system is to be used percutaneously or intra-operatively. For example, a system that is intended to be introduced percutaneously at the groin area for crossing an obstruction in a coronary vessel may utilize for a pilot wire a standard 0.014" diameter (" denotes inches) guidewire that is 80" long and have a casing with an internal diameter of 0.018", an outside diameter of 0.040" and a length of 50". The length of the distal portion of the casing can be 10" and the length of the coupling 17 can be 10". If the distal portion of the casing is made of a larger diameter wire or the pilot wire has a larger diameter the system's dimensions will increase accordingly. If the system is used in peripheral (non-coronary) blood vessels or intraoperatively where direct access to the vessel is gained surgically, the system can be made shorter.

The above mentioned and other modifications and substitutions can be made in the system and in its operation within the spirit of the invention and the scope of the following claims.

I claim:

1. A flexible guidewire system with an exposed midsection, for crossing an obstruction located in a patient's vessel, comprising in combination:
   a flexible pilot wire; and
   a flexible casing having a tubular distal portion made of a helical wire that is gated at its distal end, said distal portion being slidable and rotatable over said pilot wire, a thin elongated midsection connected to said distal portion, said midsection disposed alongside said pilot wire and is slidable along and rotatable around said pilot wire, and a proximal tubular coupling for rotating and linearly moving said casing over said pilot wire, said coupling being slidable and rotatable over said pilot wire and being connected to said midsection, wherein a section of said pilot wire that is disposed alongside said midsection of said casing is exposed.

2. As in claim 1, wherein said distal end of said flexible casing is gated by a tube section that is attached to said helical wire.

3. As in claim 1, wherein said distal end of said casing is gated by closely wound coils of said helical wire.

4. As in claim 1, wherein said midsection of said casing is made of a substantially straight wire that is a continuation of a wire of which said helical wire is made of.

5. As in claim 1, wherein said distal portion of said casing is curved.

6. As in claim 1, wherein said flexible pilot wire is a standard guidewire.

7. As in claim 1, wherein said flexible pilot wire comprises a hollow tube.

8. As in claim 1, wherein said flexible pilot wire comprises a hollow tube having a chamber attached to its distal end section, said chamber being inflatable through said hollow tube.

9. As in claim 1, wherein the flexible guidewire system is disposed in a sleeve with a biasing means to deflect the position of said casing in said vessel.

10. As in claim 9, wherein said sleeve has a curved distal end section.

11. As in claim 9, wherein said biasing means comprises a selectively inflatable chamber located at a distal end of said sleeve.

12. A method for crossing an obstruction in a patient's vessel using a flexible guidewire system with an exposed midsection that comprises a flexible pilot wire; a flexible casing with a tubular distal portion that is slidable and rotatable over said pilot wire, a thin elongated midsection disposed alongside, slidable along and rotatable around said pilot wire, and a proximal tubular coupling connected to said midsection, said coupling being slidable along and rotatable over said pilot wire and wherein a section of said pilot wire that is disposed alongside said midsection of said casing is exposed, said method comprising the following steps:

inserting a distal end of said flexible pilot wire to the vessel and, while holding the pilot wire, inserting over its proximal end the distal portion of the casing;

advancing the distal portion of the casing over the pilot wire until the proximal end of the distal portion of the casing is past the proximal end of the pilot wire and then shifting the holding point to an exposed point along the pilot wire;

continuing to advance the casing and then inserting the proximal end of the pilot wire into a distal end of the tubular coupling while continuing to hold the pilot wire at a point at which it is exposed;

advancing the coupling over the pilot wire until it is past the proximal end of the pilot wire and then shifting the holding point to a point on the pilot wire that is proximal to the coupling; and advancing and rotating said casing by rotating said coupling and thereby threading said distal portion of said casing through the obstruction.

13. As in claim 12, wherein a portion of said flexible pilot wire is inserted distally to said flexible casing, into said vessel, and provides a lever arm to angularly align said flexible casing with said vessel.

14. A method for crossing an obstruction in a patient's vessel using a flexible guidewire system with an exposed midsection that comprises a flexible pilot wire; a flexible casing with a tubular distal portion that is slidable and rotatable over said pilot wire, a thin elongated midsection disposed alongside, slidable along and rotatable around said pilot wire, and a proximal tubular coupling connected to said midsection, said coupling being slidable along and rotatable over said pilot wire and wherein a section of said pilot wire that is disposed alongside said midsection of said casing is exposed, said method comprising the following steps:

inserting a distal end of said flexible pilot wire to the vessel and, while holding the pilot wire, inserting over its proximal end the distal portion of the casing;

advancing the distal portion of the casing past the proximal end of the pilot wire and then shifting the holding point to an exposed point along the pilot wire;

continuing to advance the casing and then inserting the proximal end of the pilot wire into a distal end of the tubular coupling while continuing to hold the pilot wire at a point at which it is exposed;

advancing the coupling over the pilot wire until it is past the proximal end of the pilot wire and then shifting the holding point to a point on the pilot wire that is proximal to the coupling;

advancing and rotating said casing by rotating said coupling and thereby threading said distal portion of said casing into the obstruction, beyond the distal tip of the pilot wire, and threading it across the obstruction;

advancing the pilot wire across the obstruction; and withdrawing the casing, leaving the pilot wire in place.

15. As in claim 14 wherein withdrawing the casing leaving the pilot wire in place comprises the following steps: holding the pilot wire at a point at which it is exposed and withdrawing the coupling and then shifting the holding point to a point on the pilot wire that is distal to the distal portion of the casing; and withdrawing the distal portion of the casing.

* * * * *